(12) United States Patent
Chin et al.

(10) Patent No.: US 7,678,100 B2
(45) Date of Patent: Mar. 16, 2010

(54) APPARATUS FOR ESTABLISHING ACCESS TO THE BODY

(75) Inventors: Yem Chin, Burlington, MA (US); Clifford M. Liu, Randolph, MA (US); Benjamin J. Bottcher, Franklin, MA (US); John B. Adams, Augusta, GA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1284 days.

(21) Appl. No.: 10/949,394

(22) Filed: Sep. 27, 2004

(65) Prior Publication Data
US 2005/0049570 A1 Mar. 3, 2005

Related U.S. Application Data

(63) Continuation of application No. 09/263,897, filed on Mar. 5, 1999, now Pat. No. 6,796,976.

(60) Provisional application No. 60/081,399, filed on Apr. 10, 1998, provisional application No. 60/077,024, filed on Mar. 6, 1998.

(51) Int. Cl.
*A61M 39/02* (2006.01)
(52) U.S. Cl. .................. 604/533; 604/535; 604/166.01
(58) Field of Classification Search ............ 604/165.01, 604/165.02, 523, 533, 535, 538, 539, 166.01, 604/158, 160, 164.07, 910; 606/108; 128/DIG. 26
See application file for complete search history.

(56) References Cited

U.S. PATENT DOCUMENTS

| | | | |
|---|---|---|---|
| 2,212,334 A | 8/1940 | Wallerich | |
| 3,682,173 A | 8/1972 | Center | |
| 3,827,434 A | 8/1974 | Thompson | |
| 3,885,561 A | 5/1975 | Cami | |
| 3,890,976 A | 6/1975 | Bazell et al. | |
| 4,013,310 A * | 3/1977 | Dye | 285/110 |
| 4,111,190 A | 9/1978 | Plumridge | |
| 4,240,434 A | 12/1980 | Newkirk | |
| 4,279,252 A | 7/1981 | Martin | |
| 4,323,071 A | 4/1982 | Simpson et al. | |
| 4,354,491 A | 10/1982 | Marbry | |
| 4,485,815 A | 12/1984 | Amplatz et al. | |
| 4,554,929 A | 11/1985 | Samson et al. | |

(Continued)

FOREIGN PATENT DOCUMENTS

WO WO 99/00604 2/1999

OTHER PUBLICATIONS

Collins et al, Semiclear Percutaneous Nephrolithotomy Sheath, Journal of Endourology, vol. 11, No. Suppl 1, pp. S140, (1997).

*Primary Examiner*—Nicholas D Lucchesi
*Assistant Examiner*—Laura A Bouchelle

(57) ABSTRACT

An apparatus and method for access to the inside of a body includes a transparent sheath with a radiopaque marking and fastener for securing a guidewire or catheter. The transparent sheath permits objects located within and near the sheath to be visualized with an external imaging system. Objects located near the sheath can also be observed with an imaging device disposed inside the sheath. The radiopaque marker permits accurate positioning of the sheath in the body. The sheath can be inserted into the body over an interventional device. A fastener prevents migration of a guidewire or catheter during the procedure.

42 Claims, 16 Drawing Sheets

U.S. PATENT DOCUMENTS

| | | | |
|---|---|---|---|
| 4,571,240 A | 2/1986 | Samson et al. | |
| 4,586,921 A | 5/1986 | Berson | |
| 4,622,968 A | 11/1986 | Persson | |
| 4,643,720 A | 2/1987 | Lanciano | |
| 4,657,024 A * | 4/1987 | Coneys | 600/435 |
| 4,690,138 A * | 9/1987 | Heyden | 128/207.15 |
| 4,753,640 A | 6/1988 | Nichols et al. | 604/247 |
| 4,850,961 A * | 7/1989 | Wanderer et al. | 604/508 |
| 4,861,334 A * | 8/1989 | Nawaz | 604/539 |
| 4,895,564 A | 1/1990 | Farrell | |
| 4,990,138 A | 2/1991 | Bacich et al. | |
| 5,041,085 A | 8/1991 | Osborne et al. | |
| 5,058,580 A | 10/1991 | Hazard | |
| 5,071,408 A | 12/1991 | Ahmed | |
| 5,139,486 A * | 8/1992 | Moss | 604/164.01 |
| 5,180,376 A | 1/1993 | Fischell | |
| 5,183,464 A | 2/1993 | Dubrul et al. | |
| 5,188,605 A | 2/1993 | Sleep | |
| 5,219,335 A | 6/1993 | Willard et al. | |
| 5,242,414 A | 9/1993 | Fischell et al. | |
| 5,253,653 A | 10/1993 | Daigle et al. | |
| 5,273,527 A | 12/1993 | Schatz et al. | |
| 5,292,325 A | 3/1994 | Gurmarnik | |
| 5,300,069 A | 4/1994 | Hunsberger et al. | |
| 5,318,543 A | 6/1994 | Ross et al. | |
| 5,324,262 A | 6/1994 | Fischell et al. | |
| 5,324,269 A | 6/1994 | Miraki | |
| 5,334,185 A | 8/1994 | Giesy et al. | |
| 5,356,382 A | 10/1994 | Picha et al. | |
| 5,357,978 A | 10/1994 | Turk | |
| 5,358,493 A | 10/1994 | Schweich, Jr. et al. | |
| 5,364,355 A * | 11/1994 | Alden et al. | 604/103.09 |
| 5,368,574 A | 11/1994 | Antonacci et al. | |
| 5,380,290 A | 1/1995 | Makower et al. | |
| 5,380,304 A | 1/1995 | Parker | |
| 5,380,307 A | 1/1995 | Chee et al. | |
| 5,385,563 A | 1/1995 | Gross | |
| 5,389,087 A | 2/1995 | Miraki | |
| 5,405,354 A | 4/1995 | Sarrett | |
| 5,409,004 A | 4/1995 | Sloan | |
| 5,419,764 A | 5/1995 | Roll | |
| 5,429,617 A | 7/1995 | Hammersmark et al. | |
| 5,431,676 A | 7/1995 | Dubrul et al. | |
| 5,458,584 A | 10/1995 | Ginn et al. | |
| 5,464,394 A | 11/1995 | Miller et al. | |
| 5,484,425 A | 1/1996 | Fischell et al. | |
| 5,489,277 A | 2/1996 | Tolkoff et al. | |
| 5,496,294 A | 3/1996 | Hergenrother et al. | |
| 5,533,957 A | 7/1996 | Aldea | |
| 5,545,141 A | 8/1996 | Eld | |
| 5,571,087 A | 11/1996 | Ressemann et al. | |
| 5,613,948 A | 3/1997 | Avellanet | |
| 5,618,266 A | 4/1997 | Liprie | |
| 5,643,222 A | 7/1997 | Mahurkar | |
| 5,653,230 A | 8/1997 | Ciaglia et al. | |
| 5,658,262 A | 8/1997 | Castaneda et al. | |
| 5,685,862 A * | 11/1997 | Mahurkar | 604/194 |
| 5,702,414 A | 12/1997 | Richter et al. | |
| 5,713,894 A | 2/1998 | Murphy-Chutorian et al. | |
| 5,728,133 A | 3/1998 | Kontos | |
| 5,759,191 A | 6/1998 | Barbere | |
| 5,772,642 A | 6/1998 | Ciamacco, Jr. et al. | |
| 5,789,018 A | 8/1998 | Engelson et al. | |
| 5,795,325 A | 8/1998 | Valley et al. | |
| 5,797,882 A | 8/1998 | Purdy et al. | |
| 5,836,306 A | 11/1998 | Duane et al. | |
| 5,860,923 A | 1/1999 | Lenker et al. | |
| 5,895,378 A | 4/1999 | Nita | |
| 5,944,712 A | 8/1999 | Frassica et al. | |
| 6,007,522 A * | 12/1999 | Agro et al. | 604/264 |
| 6,027,480 A | 2/2000 | Davis et al. | |
| 6,036,682 A | 3/2000 | Lange et al. | |
| 6,096,009 A | 8/2000 | Windheuser et al. | |
| 6,152,910 A | 11/2000 | Agro et al. | |
| 6,277,107 B1 | 8/2001 | Lurie et al. | |

* cited by examiner

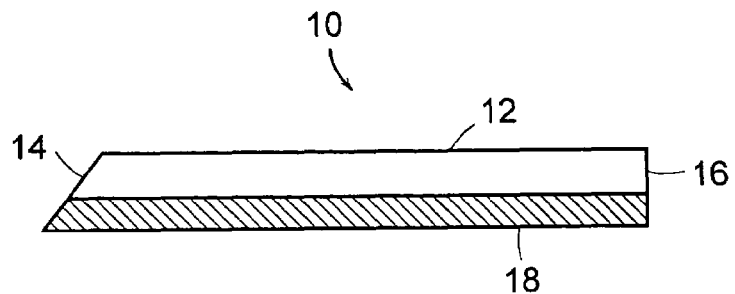
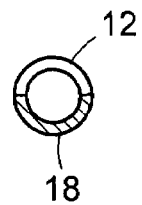
FIG. 6A   FIG. 6B
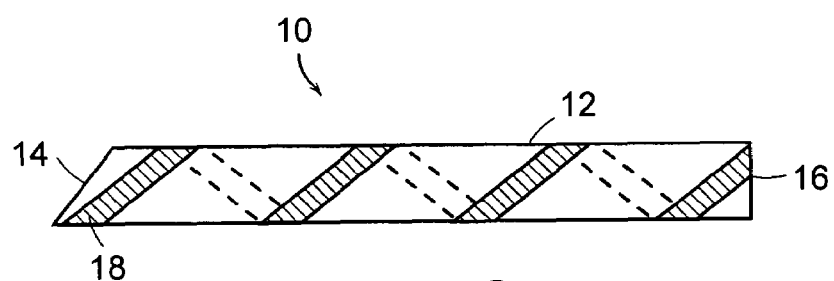
FIG. 6C
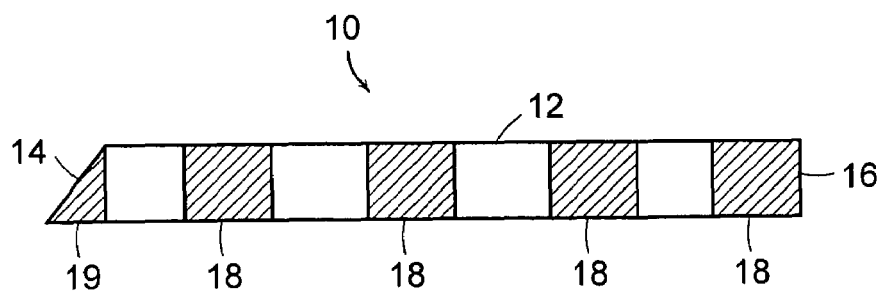
FIG. 6D

ABLE APPARATUS FOR ESTABLISHING ACCESS TO THE BODY

CROSS-REFERENCE TO RELATED APPLICATIONS

This application is a continuation of and claims priority to and the benefit of U.S. application Ser. No. 09/263,897, filed on Mar. 5, 1999, now U.S. Pat. No. 6,796,976, which claims priority to and the benefit of U.S. Provisional Application Ser. No. 60/077,024 filed on Mar. 6, 1998.

FIELD OF THE INVENTION

The present invention relates generally to an apparatus and method for percutaneous access to the inside of the body. In particular, the invention relates to a transparent sheath with a radiopaque marking at the distal end and a fastener for securing a guidewire or catheter near the proximal end of the sheath.

BACKGROUND OF THE INVENTION

Medical procedures utilizing interventional instruments (e.g., endoscopes) inserted through the skin often require preservation of the access path after the instrument is withdrawn from the body. Typically, these procedures require insertion of a sheath into the body along a guidewire previously coupled to the interventional instrument. The sheath prevents the tract established by the interventional device from closing or collapsing. One example procedure involves insertion of a dilation catheter and a guidewire along the nephrostomy tract. Once properly positioned in the body, a balloon near the distal end of the catheter is inflated to dilate the tract. A sheath is then advanced through the nephrostomy tract before the tract substantially collapses.

This procedure has inherent problems. The sheath is typically radiopaque, thus the physician cannot observe objects within or obstructed by the sheath by standard fluoroscopic techniques. In addition, optical imaging devices inserted through the sheath are unable to look out radially, thus prohibiting accurate location of objects adjacent to the sheath. Moreover, the guidewire may migrate during the exchange of instruments through the sheath, thus inhibiting placement of additional instruments along the tract.

SUMMARY OF THE INVENTION

A transparent sheath for access to the inside of a human or animal body has been developed which is useful in a variety of medical applications including, but not limited to, the exchange of instruments, drainage of fluids and removal of objects (e.g., kidney stones). The sheath can be used to provide percutaneous access to the inside of the body or it can be used in natural body orifices. Applications include urological procedures, stent delivery and laparoscopic procedures. In one embodiment, the sheath includes an elongated hollow member with a radiopaque marking at the distal end. In another embodiment, the sheath includes an elongated hollow member with at least one radiopaque marking along the length of the sheath and one or more fasteners near the proximal end of the sheath for securing other medical devices thereon such as guidewires and catheters. The sheath can be optically or fluoroscopically transparent or transparent to ultrasound. Preferably, the sheath is transparent to all three visible light (including IR and UV lights), ultrasound, and x-rays. The radiopaque marking may be disposed on the outer or inner circumference of the sheath. The radiopaque marking may be disposed on an end face of the distal end or may occupy the whole length of the sheath such as a line or spiral. One or more additional radiopaque markings may be used for identification such as in a broken line, a series or rings, or alphanumerical characters disposed along the length of the sheath (e.g., product numbers and logos). An additional radiopaque line or spiral running the length of the sheath from the distal end to the proximal end may be used to enhance visibility during the procedure.

The distal end face may be approximately perpendicular to the longitudinal axis of the sheath. In an alternative embodiment, the distal end face and longitudinal axis may define an angle less than 90° to minimize trauma to the issue during insertion and facilitate placement of the sheath.

The transparent sheath may include one or more fasteners at its proximal end for securing other medical devices thereon such as a guidewire or catheter and maintaining the sheath at a desired position within the body. The fastener may be any device or adaptation at the proximal end of the sheath which prevents other medical devices from migrating during the procedure. Example fasteners include clips, slots, or straps such as Velcro™ straps or elastic bands or a combination thereof. In one embodiment, the fastener is a retaining slot which provides an interference fit to hold the other medical device. The retaining slot may also include an opening at the end of the slot which is opposite the proximal end face of the sheath wherein the opening accepts the other medical device and restricts its longitudinal movements back and forth or migration back out of the slot through an interference fit. In yet another embodiment, a magnet is disposed adjacent to the retaining slot to secure a ferromagnetic medical device such as a guidewire.

The invention also features a method for access to the inside of a body. The method includes the steps of inserting a first medical device through a body lumen, then inserting over the second medical device such as the transparent sheath of the invention. Once the sheath is disposed at a desired location in the body, the first medical device is secured to the second medical device in the fastener. In one embodiment, the first medical device is secured by an interference fit in an opening adjacent to an end of a slot disposed at the proximal end of the second medical device, the end of the slot being opposite the proximal end face. In another embodiment, the first medical device is secured within the slot by a magnet fixed adjacent to the slot.

The method may be used for naturally existing body lumens or body lumens created by the practitioner with the use of an interventional device such as a needle or a trochar. Thus, in one embodiment, the method of the invention permits access to the inside of a body percutaneously. The percutaneous method further includes the step of inserting an interventional device into the body. The interventional device may be coupled to a guidewire or catheter. Once, the lumen is created the interventional device is decoupled from the guidewire or catheter. A transparent sheath of the invention with a fastener near its proximal end and radiopaque markings along its length is inserted into the body over the guidewire or catheter. The interventional device is then removed from the body. In one embodiment, the sheath may be inserted into the body over the guidewire after removal of the interventional device. In another embodiment, the sheath may be inserted over the interventional device before its removal.

In yet another embodiment, the methods of the invention further include the step of viewing through the first medical device objects in the body relative to a radiopaque marking at the distal end. The invention also features a method of viewing objects within or near the first medical device in a body. Objects inside or near the first medical device are viewed relative to the radiopaque marking at the distal end with an imaging device or disposed along the length of the elongated hollow body. The imaging device may be located within the first medical device or be outside of the body. In one embodiment, the imaging device is a side-viewing endoscope placed within the first medical device. In another embodiment, the imaging device is a fluoroscopic imaging system viewing from outside the body.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIGS. 6A and 6B are side and front views, respectively, of an embodiment of a transparent sheath of the invention featuring a radiopaque marking that occupies the bottom half circumference of the sheath.

FIG. 6C is a side view of an embodiment of a transparent sheath of the invention featuring a spiral radiopaque marking.

FIG. 6D is a side view of an embodiment of a transparent sheath of the invention featuring a series of rings disposed along the length of the sheath from the distal end to the proximal end.

DETAILED DESCRIPTION

Figure 1:
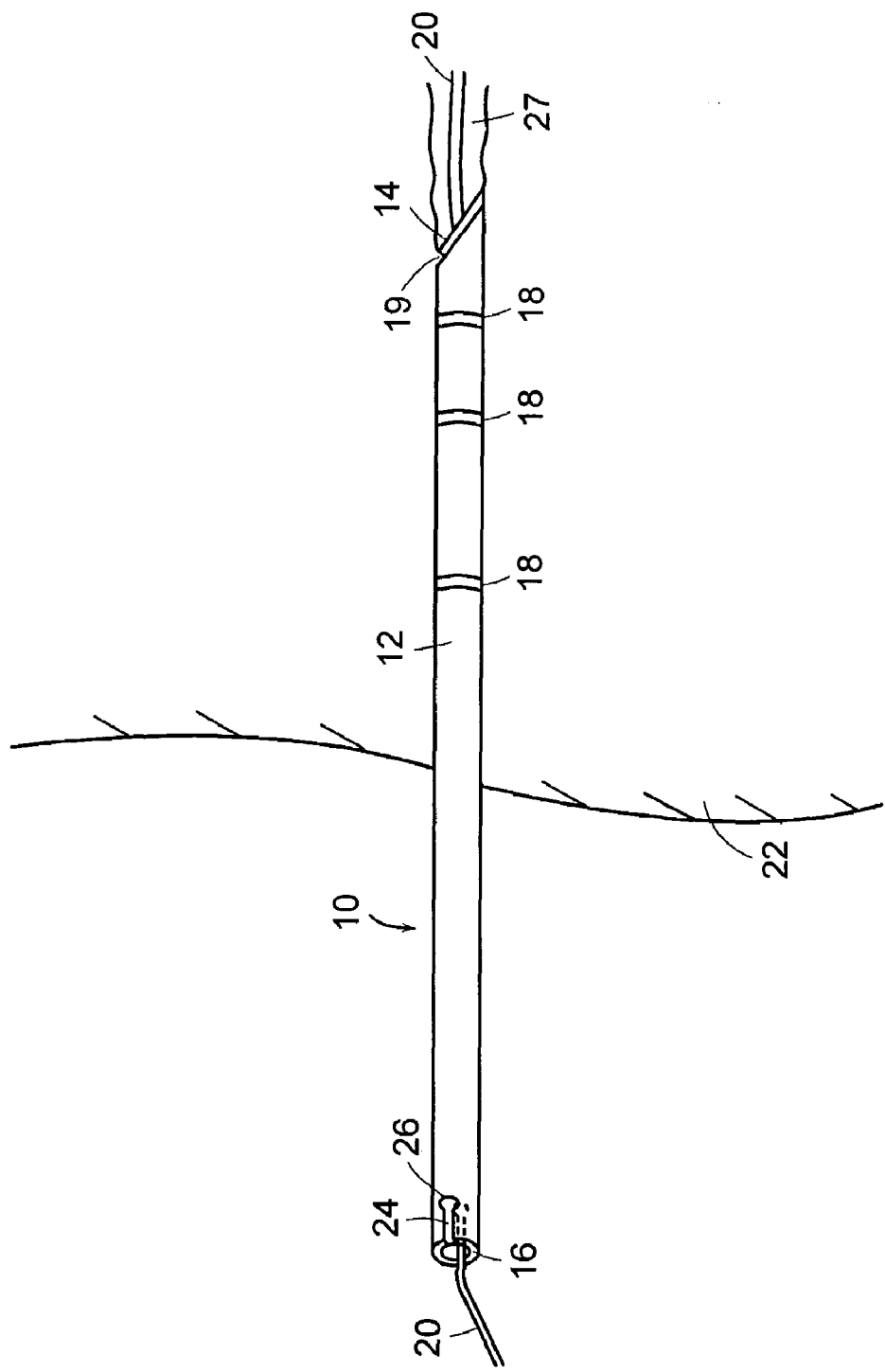
FIG. 1 is an illustration of an embodiment of a transparent sheath of the invention and guidewire inserted in a body.

Referring to FIG. 1, a transparent sheath 10 providing percutaneous access to the body 22 is partially advanced through a body tract 27 established by an interventional instrument over a guidewire 20. The sheath 10 can alternatively be used through natural body lumens for some procedures wherein percutaneous access is not required. The sheath 10 includes an elongated hollow member 12 and distal and proximal end faces 14 and 16, respectively. Radiopaque markings 18 and 19 are disposed along the elongated member 12 at known locations along the length of the elongated hollow member 12 and at the distal and 14 respectively. These multiple markings may be used as scaling features and observed during fluoroscopic imaging. Radiopaque markings 18 can also take other configurations or conformations such as lines, spirals, circles, bars, rings or alphanumeric characters to improve the visibility of the sheath 10 or identify the sheath 10. The markings may occupy the whole circumference of the sheath, such as for rings and spirals, or a portion only such as for lines, bars and other small size markings. A retaining slot 24 is adapted to receive the guidewire 20 which can be secured or locked in the opening 26 by an interference fit. The slot 24 must be narrow enough to preserve the structural rigidity of the proximal end of the sheath 10, yet be sufficiently compliant to accommodate the passage of the guidewire 20 therethrough to the opening 26. In addition, the slot 24 must be sufficiently narrow to prevent the guidewire 2 from retreating back spontaneously through the slot 24 after the guidewire 20 is position in the opening 26, yet be sufficiently compliant to permit voluntary retrieval of the guidewire or catheter 20 and withdrawal of the sheath 10 from the body track 27 once the desired medical procedure is completed.

The elongated hollow member 12 can be made from any optically clear plastic. Urethane or rigid vinyl such as polyvinylchloride (PVC) are good sheath materials owing to their flexibility. Polycarbonate materials (e.g., Plexiglas) can also be used. At least a portion of the length of the elongated member 12 is optically and/or fluoroscopically transparent, semi-transparent, or translucent to permit visualization of objects within or near the elongated member 12. Suitable material for use in the sheath of the present invention have a transmittance of at least 20% and above at a given wavelength. The transmittance (Tr) is a standardized measurement of the percentage of light intensity transmitted (Ir) through a length (m) of material normalized by the intensity of the incident light (Io): Tr=100Ir/Io The length of the path traveled by the light through the material affects the transmittance value: in the same material, the longer the path is, the lower the transmittance will be, and vice versa. Thus, high transmittance materials may be used to form sheath with thicker walls, and still provide suitable transparency for observation through the walls of the sheath. Low transmittance materials may also be used either with thinner wall, or in conjunction with higher intensity incident light or higher sensitivity light receptors.

As an illustration, FIGS. 7A-7F shows the transmittance of several transparent or semi-transparent materials suitable for use in the sheath of the present invention recorded in the visible range of 400-750 nm. To evaluate the suitability of the material for use in the sheath of the invention, transmittance may also be recorded in the wavelength of desired observation range including IR, UV or X-ray regions. As can be seen in FIGS. 7A-7F, the transmittance varies from one material to another. Also, the transmittance varies with the wavelength. A material may have a poor transmittance (below 20%) in an area of the light spectrum and a good transmittance (above 50%) in another area of the light spectrum. Observation through the sheath will be possible so long as a wavelength may be selected at which the material constituting the sheath has a transmittance of at least 20% and above. As the transmittance of the material increases clearer images may be obtained. Preferably, the wavelength will be selected in the area of highest transmittance for the material such as 40% and above, and most preferably 70% and above.

Preferable materials also maintain sufficient rigidity at body temperature to maintain the body opening propped open. Suitable material will maintain a durometer of about 50-72 Shore D at body temperature. Softer materials may be used with reinforcing materials such as, rings, coils or braids to maintain the lumen open.

The radiopaque markings 18, including a marking 19 on the distal end face 14 at the sheath 10, permit visualization of the sheath 10 inside the track 27 with a fluoroscopic imaging system and facilitate accurate positioning of the sheath 10 within the body 22. The markings 18 and 19 can be coatings made from paints, inks, or films which contain materials opaque to the imager adhered, sprayed, or painted on the sheath. For example, the radiopaque substance is preferably metal components such as metal salts, metal oxide or elemental metal or mixtures of metal components in the form of particles or powders dispersed in the coating (e.g., barium, strontium, tantalum, tungsten, gold, iridium, stainless steel and platinum). Alternatively, the particles or powders are dispersed into a portion of the elongated hollow member 12 directly at the desired location. The markings 18 and 19 may also be pieces of opaque materials such as pieces of metal or foils inserted into recesses carved into the elongated hollow member 12 or disposed on either the inner or outer surface 36 and 38, respectively, of the elongated hollow member 12 and secured into place by glue, heat and/or a covering tape.

Figure 2A:
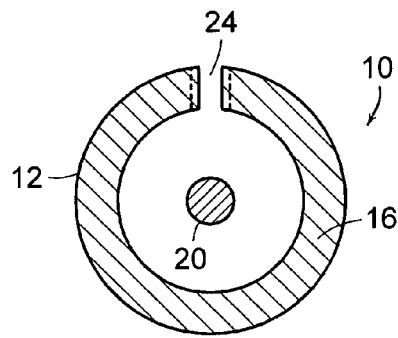
FIGS. 2A through 2D are sectional views of the proximal end of an embodiment of a transparent sheath of the invention illustrating the process of securing a guidewire to the sheath using a single retaining slot; 2A is a cross-section along the line A-A of FIG. 2B; 2B-2D are longitudinal sections.
Figure 2B:
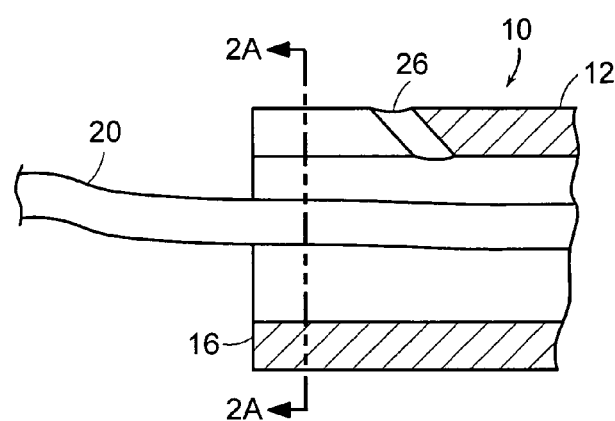

FIGS. 2A and 2B are cross and longitudinal sectional views, respectively, of the proximal end of the sheath 10 over an unsecured guidewire 20. A retaining slot 24 extends from the proximal end face 16 to a circular opening 26 in the elongated hollow member 12. A physician can secure the guidewire 20 by directing the guidewire 20 through the slot 24 to the opening 26.

Figure 2C:
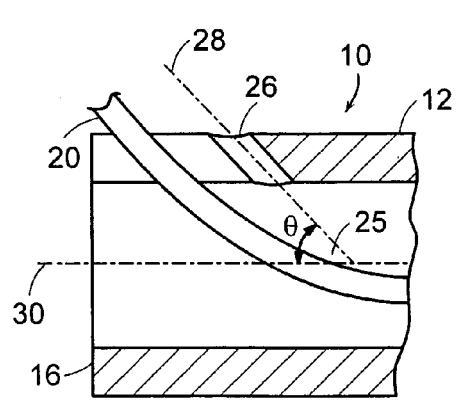
Figure 2D:
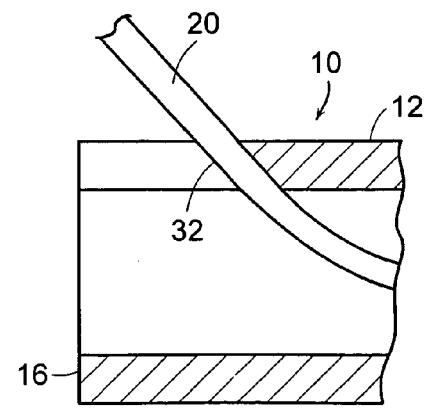

FIG. 2C illustrates a guidewire 20 partially advanced through slot 24. The opening 26 is defined about an axis 28 which forms an angle $\theta$ 25 of approximately 45° with the local longitudinal axis 30 of the sheath 10. Angle $\theta$ 25 can be any angle which prevents kinks or short radius bends in the guidewire 20. Typically, angle $\theta$ is a function of the wall thickness of the elongated member 12. The diameter of the opening 26 is selected to accommodate the diameter of the guidewire 20 and provide sufficient restraining force when the guidewire 20 is secured in the opening 26. FIG. 2D illustrates a guidewire 20 secured to the sheath 10. The guidewire 20 is held in place by compressive forces exerted by the wall 32 of the opening 26.

Figure 3A:
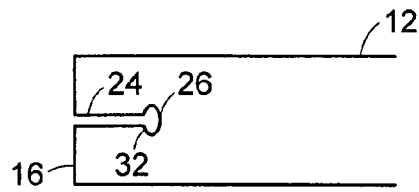
FIGS. 3A through 3I illustrate examples of fasteners at the promixal end of the transparent sheath of the invention used for securing a guidewire or catheter.
Figure 3B:
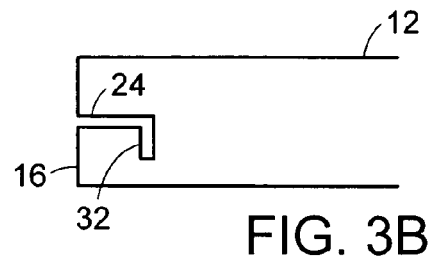
Figure 3C:
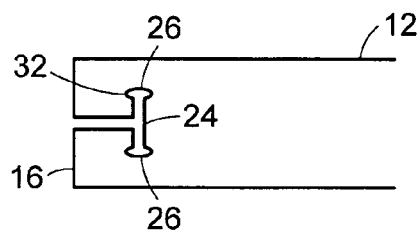
Figure 3D:
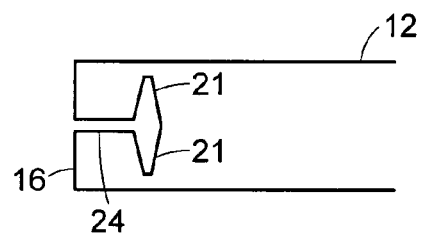
Figure 3E:
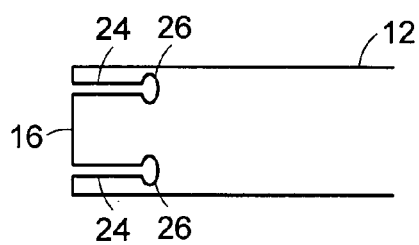
Figure 3F:
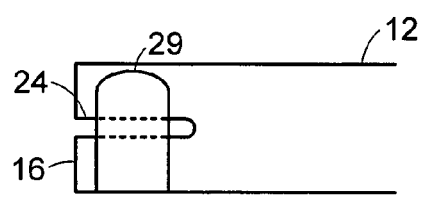
Figure 3G:
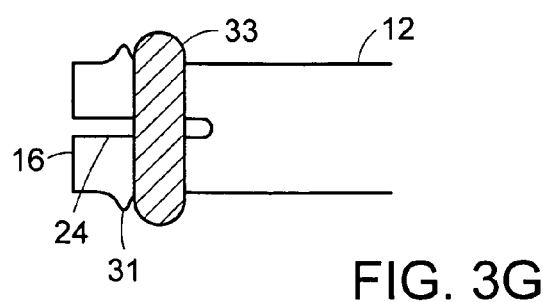

FIGS. 3A through 3I illustrate various fasteners that can be utilized to secure a guidewire 20 or catheter to a sheath. FIG. 3A shows a linear retaining slot 24 and circular opening 26 used in the embodiment illustrated in FIG. 2 FIG. 3B shows a retaining slot 24 having a longitudinal and cross-sectional portions in an L-shape. The guidewire 20 is secured by first passing it through the longitudinal portion of the slot 24 having a width slightly greater than the diameter of the guidewire 20. The guidewire 20 is then moved around the 90° bend and into the cross-sectional portion of the slot 24 having a width slightly narrower than the diameter of the guidewire 20. A compressive force exerted by the wall 32 of the slot 24 holds the guidewire 20 in place. Alternatively, the bend between the longitudinal portion and the cross sectional portion may be of an angle less than 90°. In FIGS. 3C and 3D, the slot 24 has an additional cross-sectional portions forming a T-shape with two openings 26 to permit two guidewires 20 to be secured therein. In FIG. 3D, the tapered sections 21 of the slot 24 narrow to a width which is less than the diameter of the guidewire 20 thus holding it in place by an interference fit. Alternatively, one or both of the cross-sectional portions may form an angle with the longitudinal portion less than 90°. FIG. 3E shows two separate slots 24 for holding two guidewires. FIG. 3F shows a slot 24 over which a strap of self-adhesive material 29 is circumferentially arranged. Alternatively, the strap 29 can be fabricated from an interlocking material such as Velcro™. In FIG. 3G, a grommet 33 is shown in a position for securing the guidewire 20 at the end of the slot 24. The guidewire 20 first is moved to the end of the slot 24. next, the grommet 33 is placed onto the elongated member 12 near the proximal end face 16 and slipped over an annular ridge 31. In this position, compressive force exerted by the grommet 33 keeps the guidewire 20 clamped at the end of the slot 24.

Figure 3H:
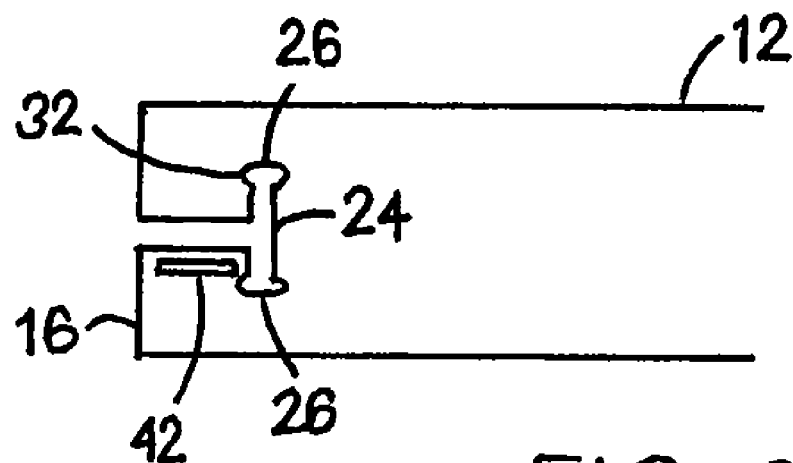
Figure 3I:
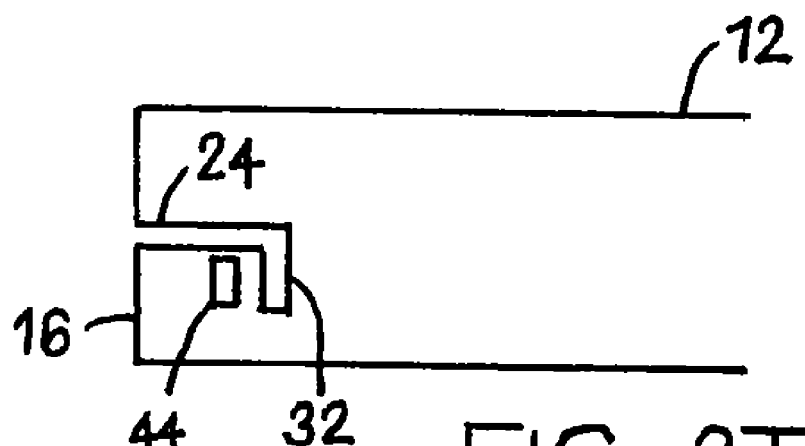

It should be understood in conjunction with the descriptions of fasteners for securing a guidewire described above that multiple retaining slots 24 can be used to secure multiple guidewires 20 to the sheath 10. Furthermore, it should be understood that safety wires, catheters, and other medical instruments having geometries resembling guidewires can be similarly secured to the sheath 10. In addition, clips 44 (as illustrated in FIG. 3I), latches, magnets 42 (as illustrated in FIG. 3H), small locking devices and other fasteners can be integrated or attached to the proximal end of the sheath 10 to secure guidewires, in place of, or in combination with, those described above.

Figure 4A:
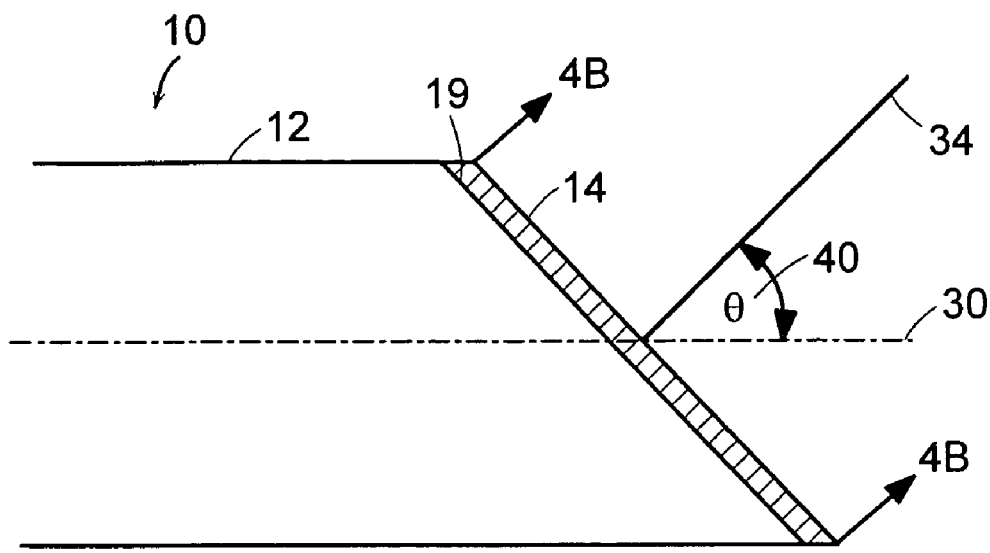
FIGS. 4A through 4D are illustrations of the distal end of a transparent sheath having a radiopaque marking on the distal end face 4A, 4C, and 4D are side views, and 4B is a front view.
Figure 4B:
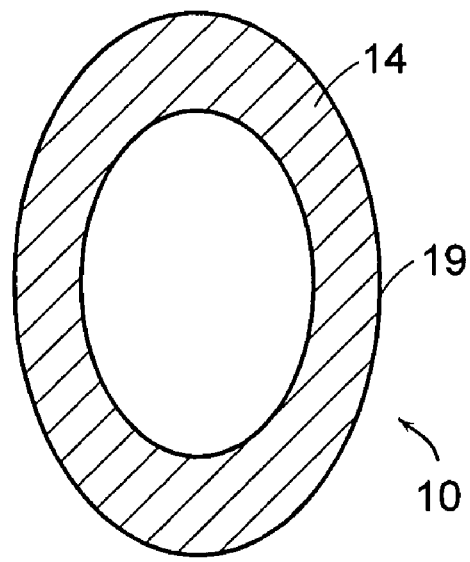
Figure 4C:
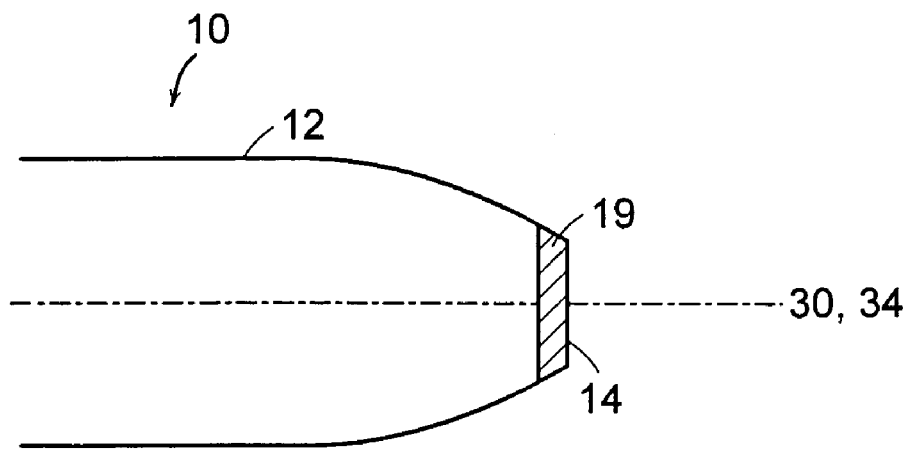
Figure 4D:
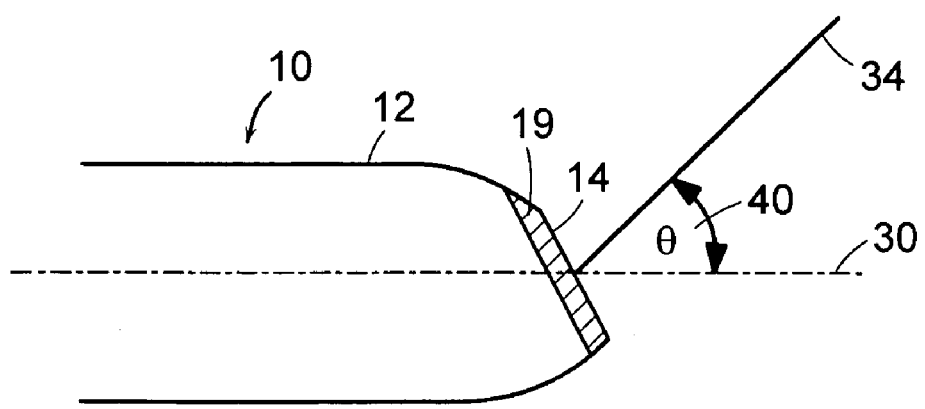

FIGS. 4A and 4B are lateral and front views of the distal end of the sheath 10, respectively. The normal 34 to the end face 14 defines a tip angle $\phi$ 40 of approximately 45° to facilitate a traumatic advancement of the sheath 10 within the body 22. Angle $\phi$ 40 can range anywhere between 0° and 90° and can be selected according to the specific procedure for which the sheath 10 will be employed. Alternatively, the sheath 10 can be tapered near the end face 14 to reduce trauma as shown in FIGS. 4C and 4D. A radiopaque marking 19 covers the elliptically-shaped surface of the distal end face 14 thus providing accurate information on the position of the distal end of the sheath 10 within the body 22 when observed with a fluoroscopic imaging system. The marking 19 can extend around the edge of the distal end face 14 and onto the adjacent outer wall of the elongated member 12 so that the distal end of the sheath 10 can still be observed when the axis 30 of the elongated hollow member 12 is perpendicular to the viewing axis of the fluoroscopic imager.

Figure 5A:
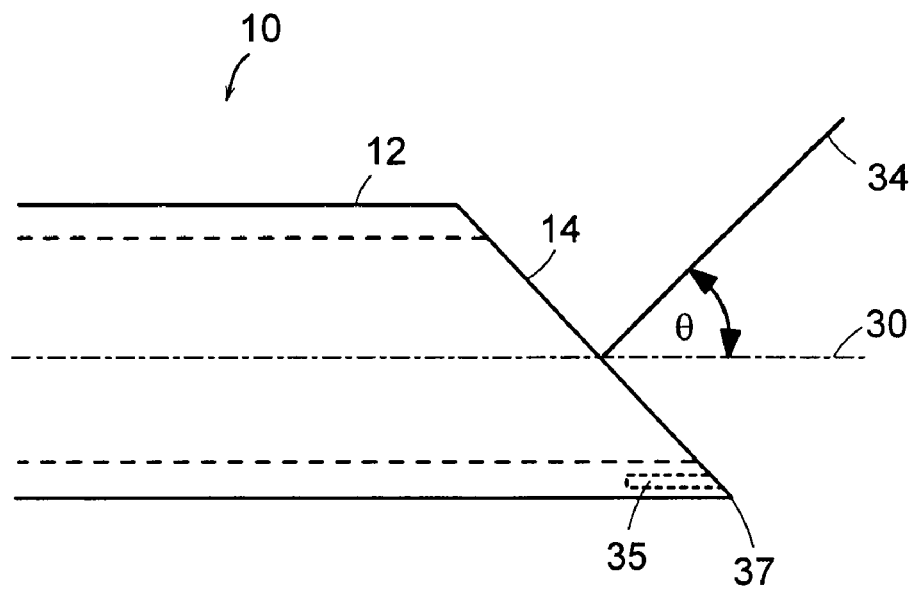
FIGS. 5A and 5B are side and front views, respectively, of the distal end of an embodiment of a transparent sheath of the invention having a small radiopaque marking near the extreme distal end of a 45° distal end face.
Figure 5B:
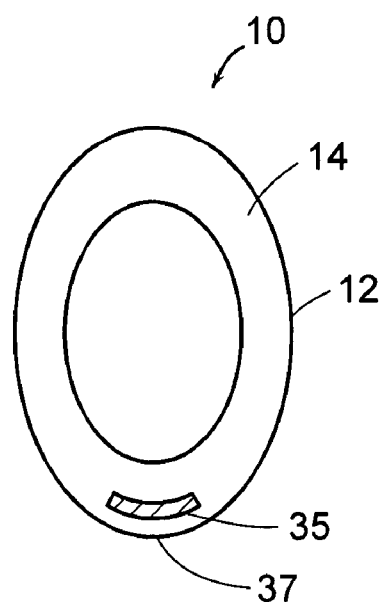
Figure 7A:
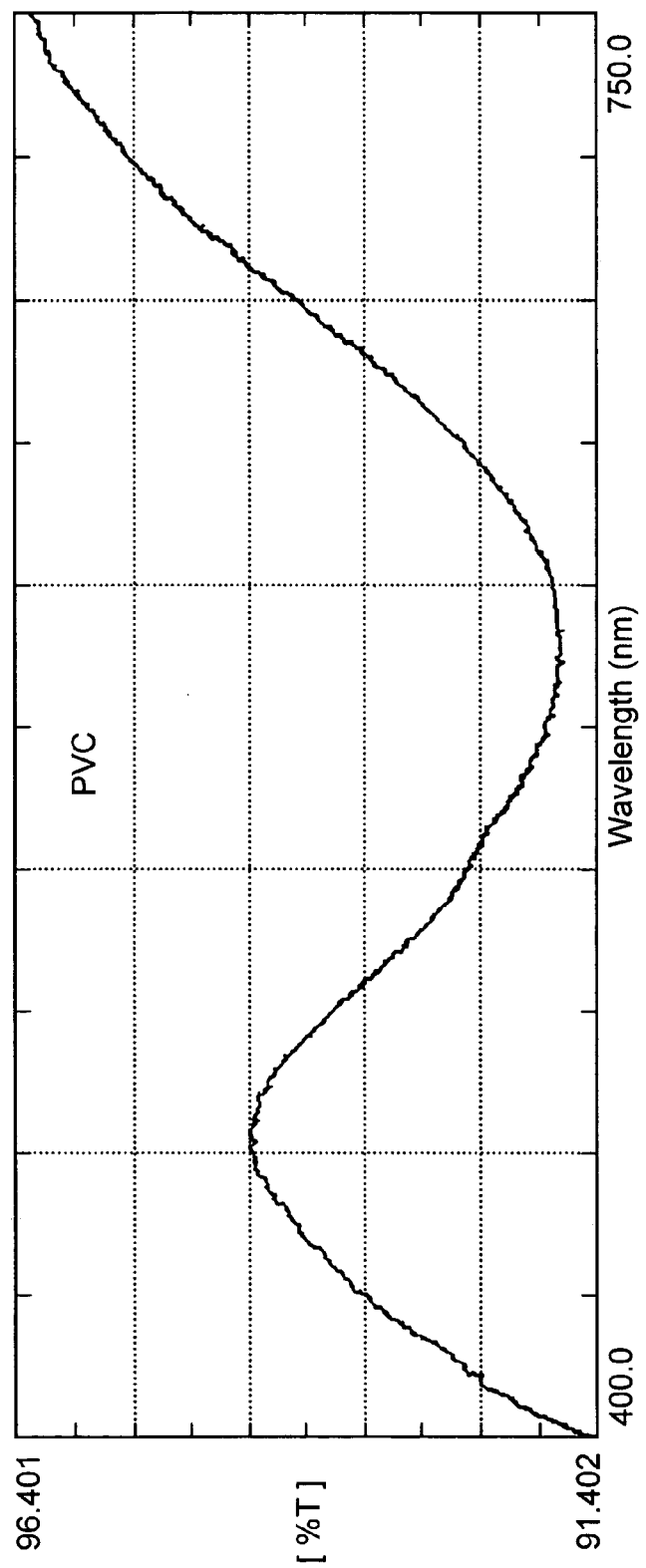
FIGS. 7A-7F are plots of the transmittance of visible light ranging from 400 to 750 nm through pieces of transparent or translucent polymers: A, polyvinyl chloride (PVC) 0.022 in thick; B, 0.017 PVC 0.017 in thick; C, Tecoflex™ 0.022 in thick; D: Teflon (TFE) 0.026 in thick; E, Nylon 0.030 in thick; F, Polyethylene (PE) 0.030 in thick.
Figure 7B:
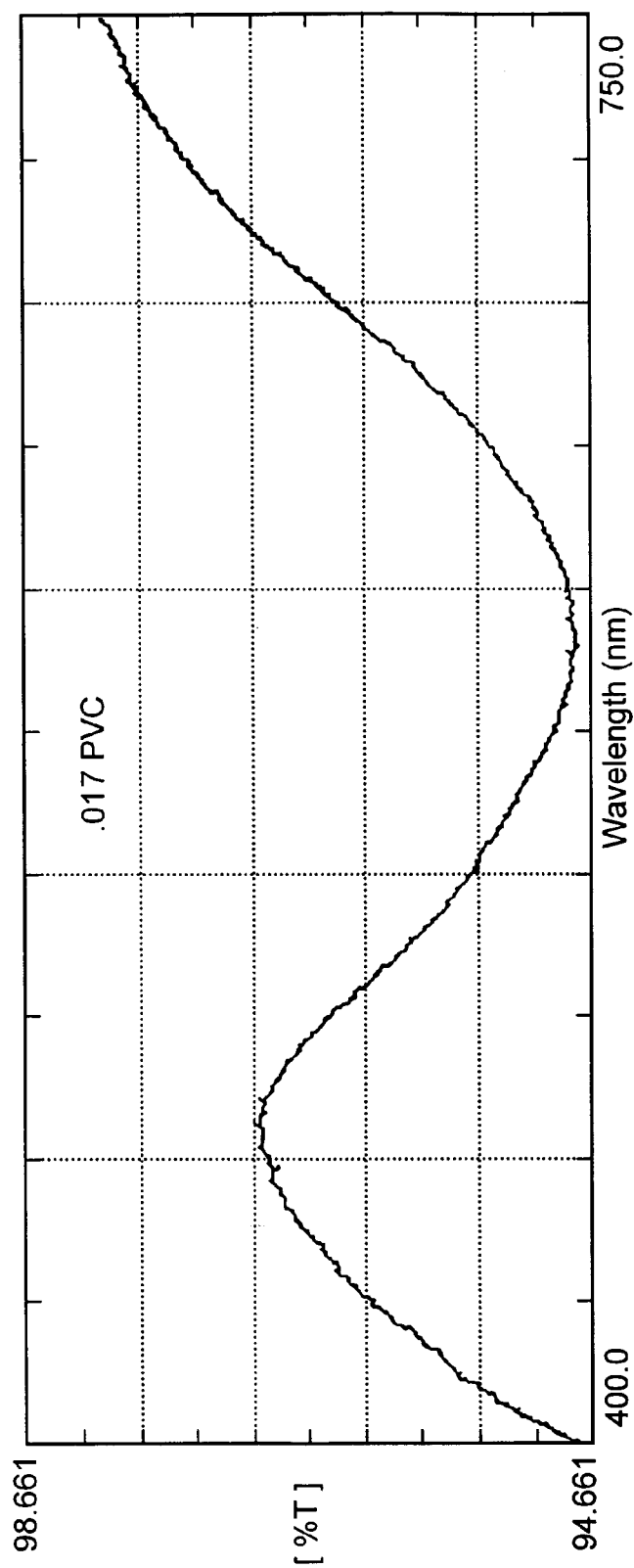
Figure 7C:
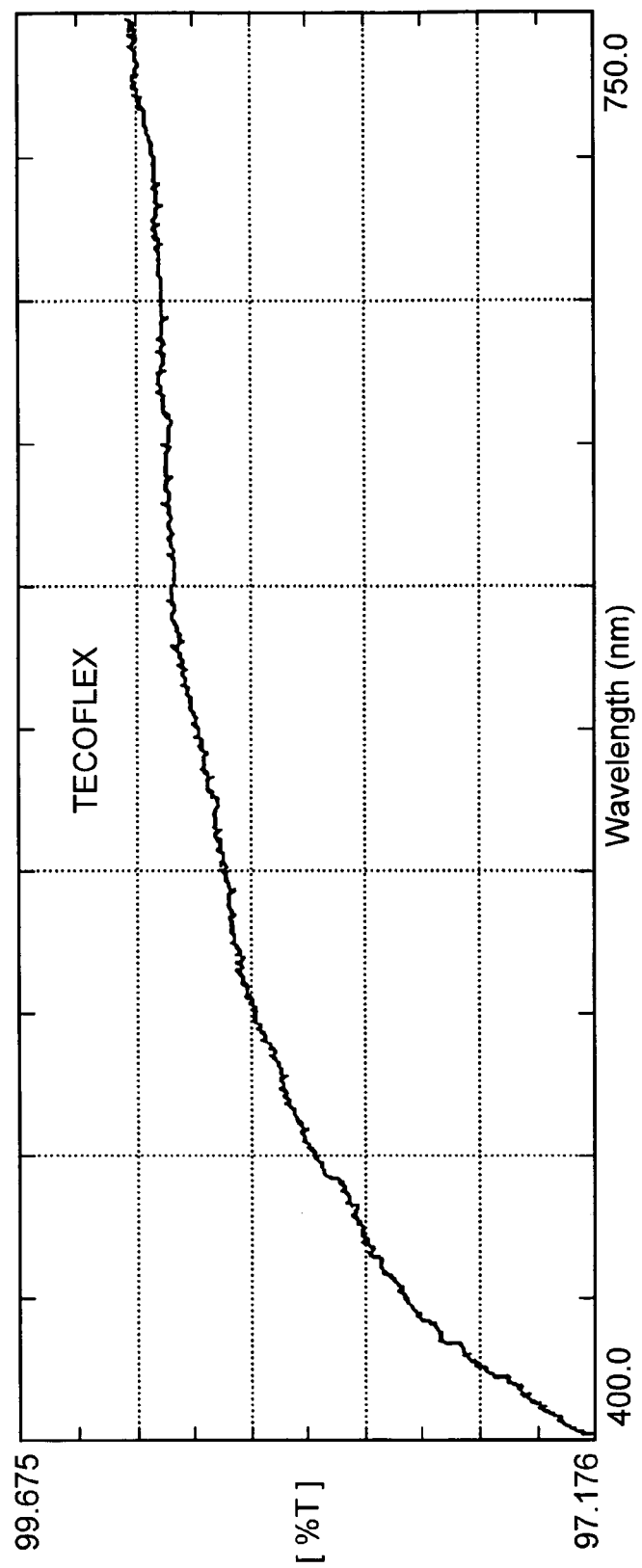
Figure 7D:
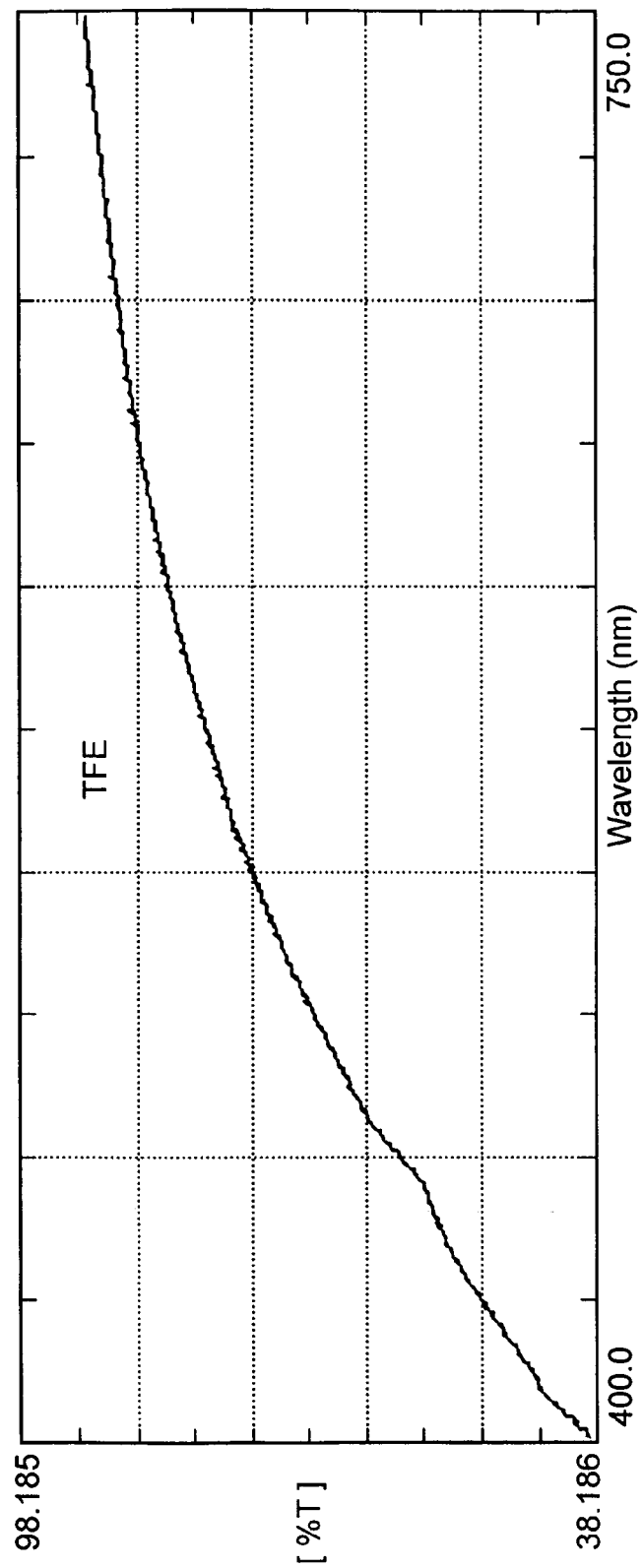
Figure 7E:
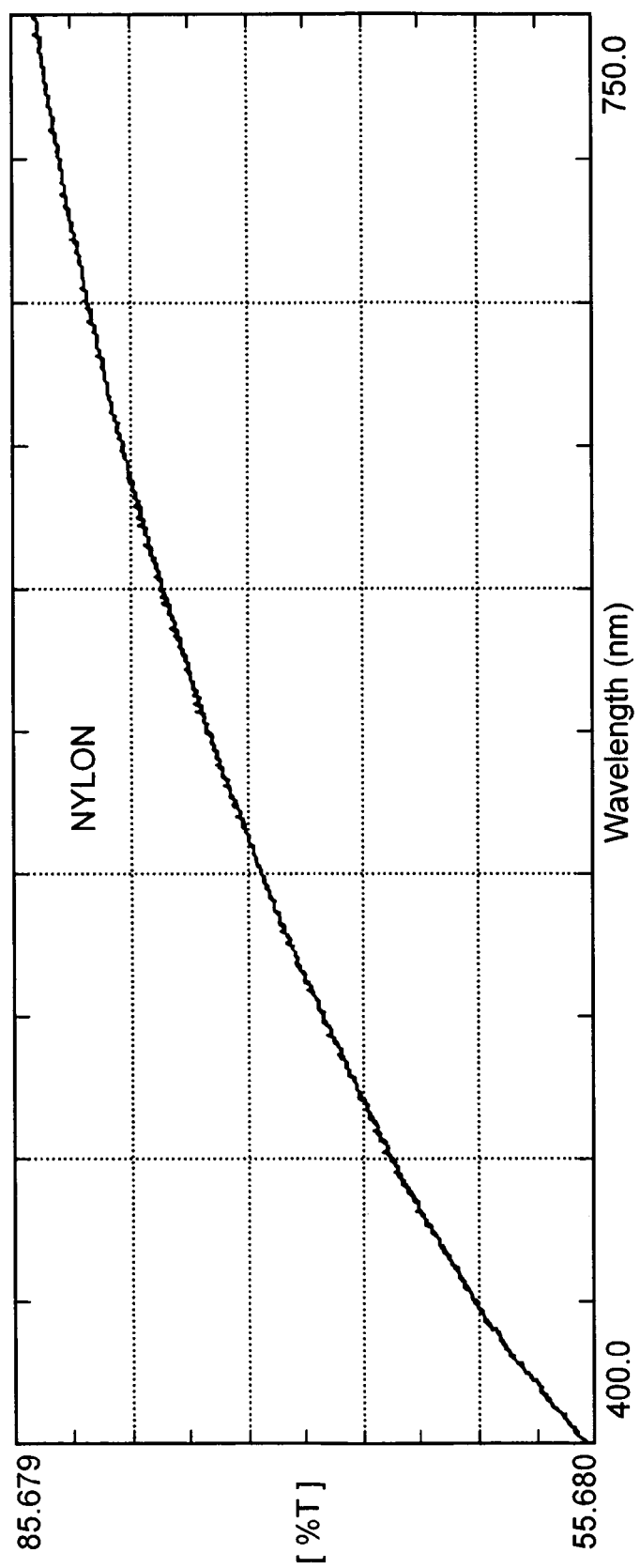
Figure 7F:
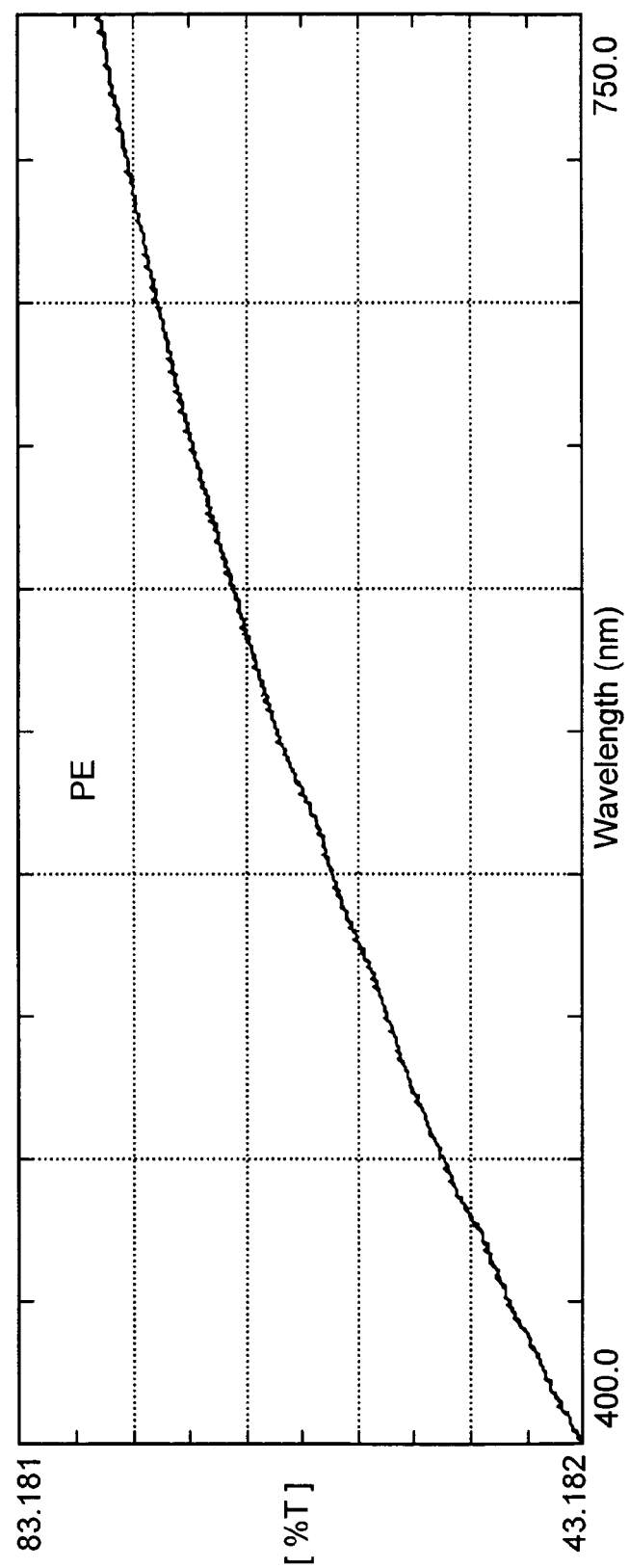

Referring to FIGS. 5A and 5B, accurate knowledge of the location of the extreme distal end 37 within the body 22 is necessary to avoid injury to internal organs. Thus, a small radiopaque marking 35 embedded in the elongated member 12 near the extreme distal end 37 can be more advantageous than larger marking configurations such as band or stripe. Encapsulation or thermal bonding techniques can be used to dispose the small radiopaque marking 35 in the elongated hollow member 12. Alternatively, the marking 35 may be secured into a recess with glue or covering tape.

FIGS. 6A-6D show alternative embodiments of the sheath having various configurations of radiopaque markings. In FIGS. 6A and 6B the radiopaque marking 18 is a line that extends from the distal end face 14 to the proximal end face 16 and occupy the bottom half circumference of the elongated hollow member 12. In FIG. 6C, the radiopaque marking 18 is a spiral line that extends form the distal end face 14 to the proximal end face 16. In FIG. 6D, the radiopaque markings 18 and 19 are a series of rings distributed along the length of the sheath at regular intervals.

Figure 8:
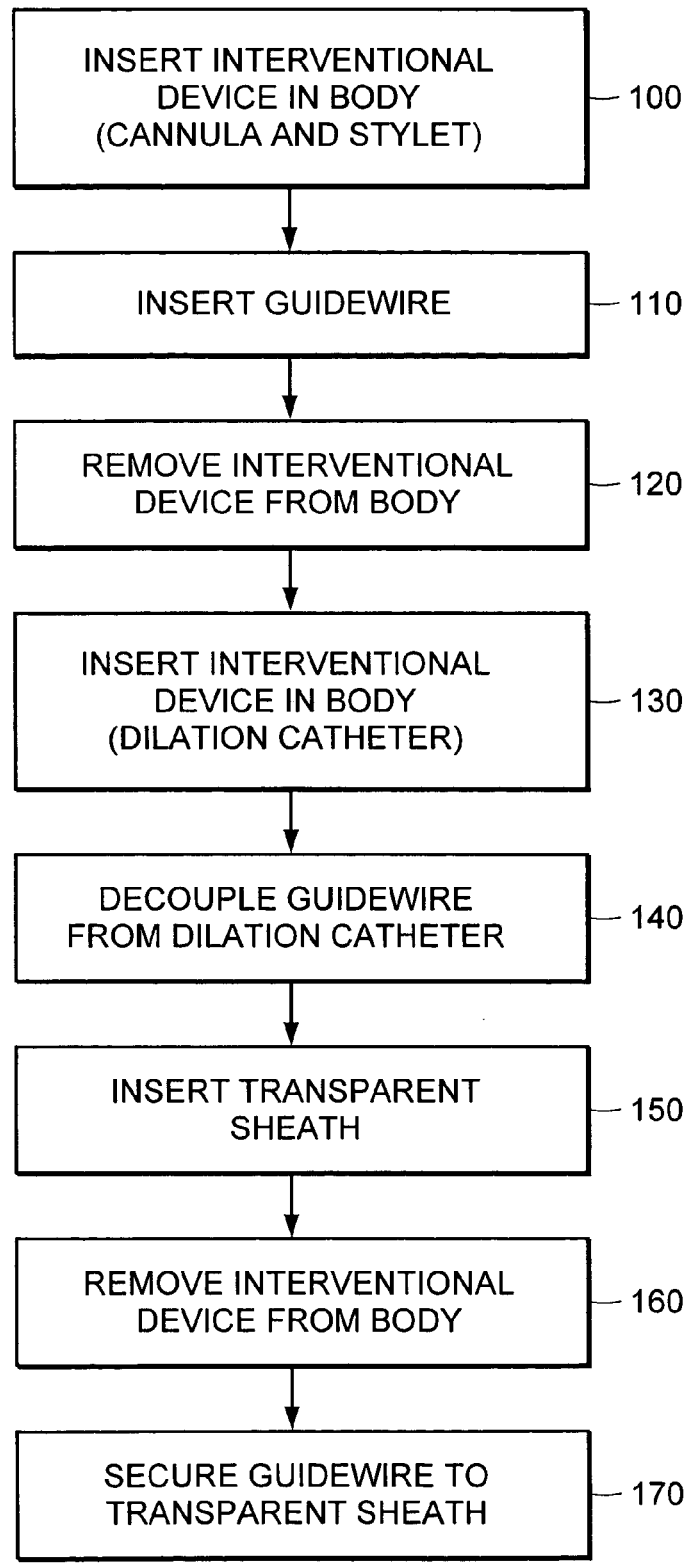
FIG. 8 is a flowchart of a method of access to the inside of a body according to the invention.

Referring to the flowchart of FIG. 8, a method for access to the inside of a body is shown as a series of steps. In step 100, an interventional device (e.g., a cannula and stylet) is inserted into a body to create an access tract. In step 110, a guidewire or catheter is inserted through the interventional device. The interventional device is removed in step 120, leaving the guidewire in place. Depending on the requirements of the procedure, step 120 can be performed before step 110 is performed. In some procedures, it is desirable to insert a second guidewire (e.g., safety wire) after removal of the interventional device. A dilation catheter (interventional device) coupled to the guidewire is then used to expand the tract to accommodate larger instrumentation, as indicated in step 130. The guidewire is detached, from the dilation catheter in step 140. In step 150, a transparent sheath having at least one fastener at its proximal end is inserted into the tract over the dilation catheter. The dilation catheter is withdrawn from the body in step 160. Depending on the requirements of the procedure, step 160 can be performed before step 150 is performed. The guidewire is then secured to the sheath in step 170. The sheath can include various types of fasteners, including retaining slots, clips, latches, magnets, small locking devices or other fasteners. The sheath can also include a radiopaque marking to aid in its positioning and for reference when viewing objects within the body.

Figure 9:
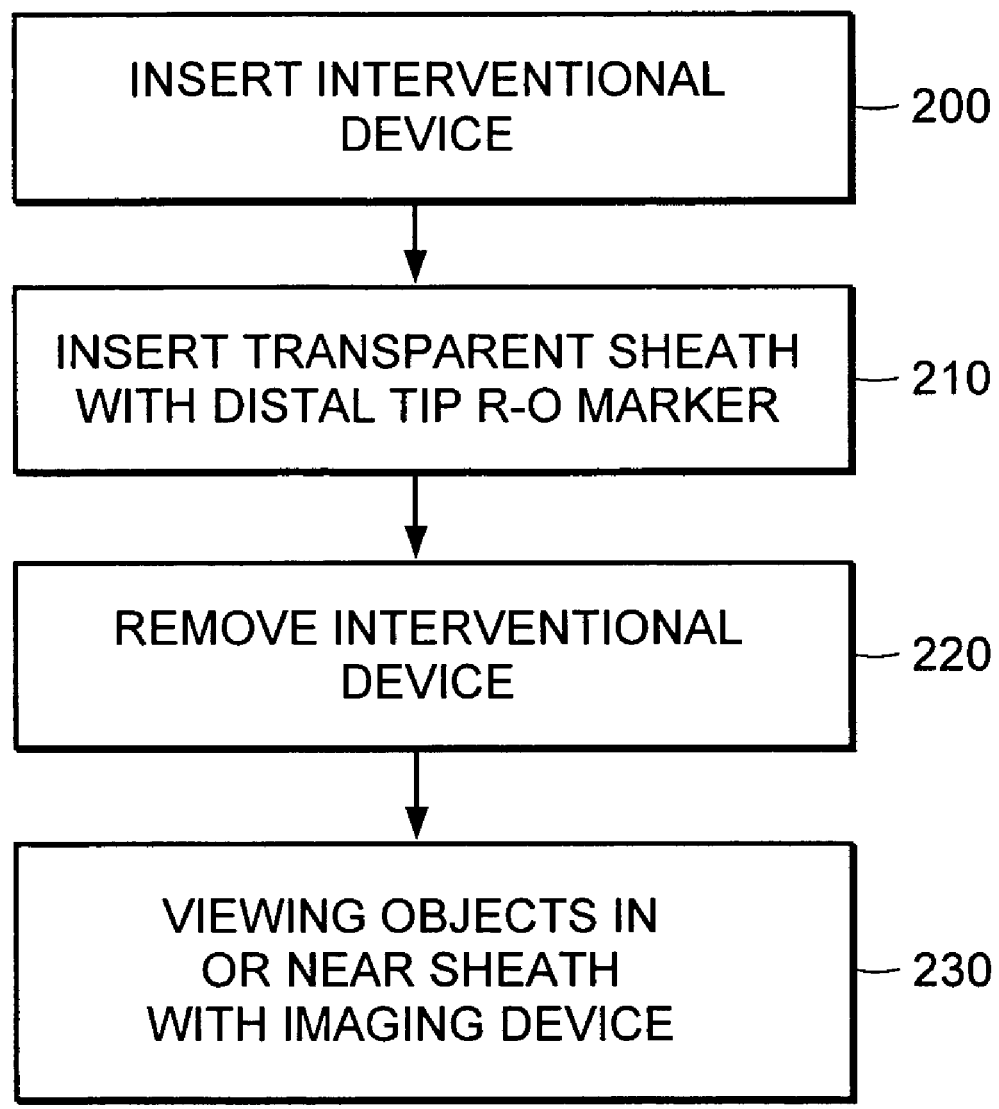
FIG. 9 is a flowchart of a method of viewing objects within or adjacent to a sheath within a body according to the invention.

Referring to the flowchart of FIG. 9, a method for viewing objects within or near a sheath within a body is shown as a series of steps. In step 200, an interventional device (e.g., dilation catheter) is inserted into the body. In step 210, a transparent sheath with a radiopaque marking is inserted into the body over the interventional device. The interventional device is removed from the body according to step 220. In some procedures it is preferable to remove the interventional device before insertion of the transparent sheath. A guidewire can be inserted along the tract created by the interventional device and can be secured to the sheath by a fastener disposed near the proximal end of the sheath. In step 230, objects located in or near the sheath are observed relative to the sheath using an imaging device. The imaging device can be a viewing catheter which can include miniature imaging optics and/or a solid state imager disposed at the distal end of the catheter. The imaging device can be located substantially within the sheath and used for forward-viewing or side-viewing (i.e., radial-viewing) through the wall of the sheath. In some instances, the sheath may act as a magnifier of nearby objects. The image information is transmitted via fiber optics or electrical conductor to processing and display optics near the proximal end of the catheter. A forward-viewing or side viewing endoscope can be also be used to view objects located within or near the sheath. Alternatively, a fluoroscopic imaging system external to the body can be used to view objects relative to the sheath.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

We claim:

1. A sheath for maintaining patency of an opening in a human or animal body, the sheath comprising:
an elongated member configured to maintain the patency of an opening in the human or animal body, the elongated member having a lumen configured to receive at least a portion of a medical device such that the medical device may be moved from a first position to a second position, the elongated member defining a slot in communication with the lumen, the elongated member including a clip disposed adjacent at least a portion of the slot, the slot configured to engage the medical device when the medical device is passed through the slot and is in the second position to restrict longitudinal motion of the medical device with respect to the elongated member, the clip configured to engage the medical device when the medical device is in the second position, the elongated member being made of a transparent material.

2. The sheath of claim 1, wherein the transparent material is a material that is transparent to visible light.

3. The sheath of claim 1, wherein the transparent material is a material that is transparent to x-rays.

4. The sheath of claim 1, wherein the elongated member includes at least one radiopaque marker.

5. The sheath of claim 1, wherein the elongated member includes at least one radiopaque marker disposed on a distal end portion of the elongated member.

6. The sheath of claim 1, wherein the elongated member includes at least one radiopaque marker that is disposed on and parallel to a length of the elongated member.

7. The sheath of claim 1, wherein the medical device is a guidewire.

8. The sheath of claim 1, wherein the medical device is a catheter.

9. The sheath of claim 1, wherein the elongated member defines a longitudinal axis, the elongated member including a distal end face, the distal end face and the longitudinal axis defining an angle of about 90 degrees.

10. The sheath of claim 1, wherein the elongated member defines a longitudinal axis, the elongated member including a distal end face, the distal end face and the longitudinal axis defining an angle of less than 90 degrees.

11. The sheath of claim 1, wherein the slot includes a "T" shaped portion.

12. The sheath of claim 1, wherein the slot includes an "L" shaped portion.

13. The sheath of claim 1, wherein the lumen is configured to receive at least a portion of an imaging device.

14. The sheath of claim 1, wherein the elongated member includes a band disposed proximate to the slot, the band configured to engage the medical device when the medical device is in the second position.

15. The sheath of claim 1, wherein the clip is configured to directly engage the medical device when the medical device is in the second position.

16. A sheath for maintaining patency of an opening in a human or animal body, the sheath comprising:
an elongated member configured to maintain the patency of an opening in the human or animal body, the elongated member defining a proximal end portion, a distal end portion, and a lumen extending from the proximal end portion to the distal end portion, the lumen being configured to receive at least a portion of a medical device such that the medical device may be moved from a first position where the medical device passes through a portion of the lumen defined by the proximal end portion of the elongated member to a second position, the elongated member including a clip disposed on the proximal end portion of the elongated member at least partially adjacent a slot defined by the proximal end portion of the elongated member, the slot being in communication with the lumen, the clip being configured to engage the medical device when the medical device is in the second position and a portion of the medical device is passed through the slot to restrict longitudinal motion of the medical device with respect to the elongated member.

17. The sheath of claim 16, wherein the elongated member is made of a material that is transparent to visible light.

18. The sheath of claim 16, wherein the elongated member is made of a material that is transparent to x-rays.

19. The sheath of claim 16, wherein the elongated member includes at least one radiopaque marker.

20. The sheath of claim 16, wherein the medical device is a guidewire.

21. The sheath of claim 16, wherein the medical device is a catheter.

22. The sheath of claim 16, wherein the clip is configured to directly engage the medical device when the medical device is in its second position.

23. A sheath for maintaining patency of an opening in a human or animal body, the sheath comprising:
   an elongated member configured to maintain the patency of an opening in the human or animal body, the elongated member defining a proximal end portion, a distal end portion, and a lumen extending from the proximal end portion to the distal end portion, the lumen being configured to receive at least a portion of a medical device such that the medical device may be moved from a first position where the medical device passes through a portion of the lumen defined by the proximal end portion of the elongated member to a second position, the elongated member including a band disposed over a portion of a slot defined by the proximal end portion of the elongated member, the slot being in communication with the lumen, the band being configured to engage the medical device when the medical device is in the second position and a portion of the medical device is passed through the slot to restrict longitudinal motion of the medical device with respect to the elongated member.

24. The sheath of claim 23, wherein the elongated member is made of a material that is transparent to visible light.

25. The sheath of claim 23, wherein the elongated member is made of a material that is transparent to x-rays.

26. The sheath of claim 23, wherein the elongated member includes at least one radiopaque marker.

27. The sheath of claim 23, wherein the band is configured to directly engage the medical device when the medical device is in the second position.

28. A sheath for maintaining patency of an opening in a human or animal body, comprising:
   an elongated hollow member having sufficient rigidity to maintain patency of the opening of the body, the elongated hollow member including a transparent material that permits imaging through the wall of the elongated hollow member, the transparent material being transparent to visible light, the elongated hollow member having a proximal end portion, a distal end portion, and a radiopaque marking, the proximal end portion including a proximal end face, the elongated hollow member allowing movement of a medical device from a first position where the medical device passes through the proximal end face to a second position where longitudinal motion of the medical device is restricted, the elongated hollow member defining a retaining slot to engage the medical device when in the second position to restrict longitudinal motion of the medical device, the elongated hollow member including a clip disposed at least partially adjacent the slot, the clip configured to engage the medical device when in the second position, the elongated hollow member including a magnet disposed adjacent to the slot.

29. The sheath of claim 28, wherein the slot provides an interference fit with the medical device to restrict longitudinal motion of the medical device with respect to the elongated member.

30. The sheath of claim 28, wherein the radiopaque marking is a radiopaque line disposed on and parallel to a length of the elongated hollow member.

31. The sheath of claim 28, further comprising:
   a plurality of radiopaque markings.

32. The sheath of claim 28, wherein the elongated hollow member is configured to be viewed with an imaging device to view objects disposed within or adjacent to the elongated hollow member.

33. The sheath of claim 28, wherein the elongated hollow member is configured to be viewed with an imaging device to view objects disposed within or adjacent to the elongated hollow member, the imaging device being a side-viewing endoscope.

34. The sheath of claim 28, wherein the elongated hollow member is configured to be viewed with an imaging device to view objects disposed within or adjacent to the elongated hollow member, the imaging device being a fluoroscopic imaging system external to the body.

35. The sheath of claim 28, wherein the radiopaque marking is disposed at a distal end of the elongated hollow member.

36. The sheath of claim 28, wherein the radiopaque marking is disposed at a distal end of the elongated hollow member, the elongated hollow member is configured to be viewed with an imaging device to view objects with respect to the radiopaque marking.

37. The sheath of claim 28, wherein the transparent material is transparent to x-rays.

38. The sheath of claim 28, wherein at least one of the clip or the magnet is configured to directly engage the medical device when the medical device is in the second position.

39. A sheath for maintaining patency of an opening in a human or animal body, comprising:
   an elongated hollow member having sufficient rigidity to maintain patency of the opening of the body, the elongated hollow member including a transparent material that permits imaging through the wall of the elongated hollow member, the transparent material being transparent to visible light, the elongated hollow member having a proximal end portion, a distal end portion, and a radiopaque marking, the proximal end portion including a proximal end face, the elongated hollow member allowing movement of a medical device from a first position where the medical device passes through the proximal end face to a second position where longitudinal motion of the medical device is restricted, the elongated hollow member comprising a band to engage the medical device when in the second position and when a portion of the medical device is passed through a slot defined by the proximal end portion of the elongated hollow member to restrict longitudinal motion of the medical device, the band being disposed over a portion of the slot, the slot being in communication with a lumen defined by the elongated hollow member.

40. The sheath of claim 39, further comprising:
   a plurality of radiopaque markings.

41. The sheath of claim 39, wherein the transparent material is transparent to x-rays.

42. The sheath of claim 39, wherein the band is configured to directly engage the medical device when the medical device is in the second position.

* * * * *